(12) United States Patent
Stout et al.

(10) Patent No.: US 8,932,259 B2
(45) Date of Patent: Jan. 13, 2015

(54) CATHETER ASSEMBLY

(75) Inventors: Marty L. Stout, South Jordan, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 353 days.

(21) Appl. No.: 12/880,649

(22) Filed: Sep. 13, 2010

(65) Prior Publication Data

US 2012/0065612 A1 Mar. 15, 2012

(51) Int. Cl.
*A61M 5/178* (2006.01)
*A61M 25/06* (2006.01)
*A61M 39/06* (2006.01)

(52) U.S. Cl.
CPC ..... *A61M 25/0606* (2013.01); *A61M 2039/066* (2013.01); *A61M 39/06* (2013.01); *A61M 2039/062* (2013.01); *A61M 2039/064* (2013.01); *A61M 2039/0626* (2013.01); *A61M 39/0606* (2013.01); *A61M 39/0693* (2013.01); *A61M 25/0693* (2013.01); *A61M 2039/0686* (2013.01); *A61M 2039/0633* (2013.01)
USPC ............ 604/167.02; 604/167.03; 604/167.04; 604/168.01; 604/537

(58) Field of Classification Search
CPC ..................... A61M 39/0693; A61M 25/0693; A61M 2039/064; A61M 2039/066; A61M 39/045
USPC ............ 604/167.02, 167.03, 167.04, 168.01, 604/537
See application file for complete search history.

(56) References Cited

U.S. PATENT DOCUMENTS

| | | |
|---|---|---|
| 4,387,879 A | 6/1983 | Tauschinski |
| 4,449,693 A | 5/1984 | Gereg |
| 4,758,225 A | 7/1988 | Cox et al. |
| 4,842,591 A | 6/1989 | Luther |
| 4,874,377 A | 10/1989 | Newgard et al. |
| 4,917,668 A | 4/1990 | Haindl |
| 4,935,010 A | 6/1990 | Cox et al. |
| 4,950,257 A | 8/1990 | Hibbs et al. |
| 5,041,097 A | 8/1991 | Johnson |
| 5,053,014 A | 10/1991 | Van Heugten |
| 5,062,836 A | 11/1991 | Wendell |
| 5,064,416 A | 11/1991 | Newgard et al. |
| 5,084,023 A | 1/1992 | Lemieux |

(Continued)

FOREIGN PATENT DOCUMENTS

| | | |
|---|---|---|
| CA | 2133053 A1 | 3/1995 |
| DE | 202009009602 U1 | 10/2009 |

(Continued)

OTHER PUBLICATIONS

Silva, Elson, Email Regarding "Respecting Hydrology Science and IP Rights—US Pat. Application 20110130728," pp. 1-6, Jun. 2, 2011.

*Primary Examiner* — Emily Schmidt
(74) *Attorney, Agent, or Firm* — Jeanne Lukasavage; Craig Metcalf; Kirton McConkie

(57) ABSTRACT

A catheter assembly is disclosed having a catheter adapter and a needle hub. The catheter adapter has an inner lumen with a septum located within the inner lumen. An introducer needle is inserted through the inner lumen. A septum activator also located within the inner lumen, such that a distal end of the septum activator contacts the septum. The septum activator has an internal cavity and a cavity seal forming a surface of the internal cavity.

15 Claims, 12 Drawing Sheets

(56) References Cited

U.S. PATENT DOCUMENTS

| | | |
|---|---|---|
| 5,085,645 A | 2/1992 | Purdy et al. |
| 5,108,374 A | 4/1992 | Lemieux |
| 5,127,905 A | 7/1992 | Lemieux |
| 5,154,703 A | 10/1992 | Bonaldo |
| 5,156,596 A | 10/1992 | Balbierz et al. |
| 5,234,410 A | 8/1993 | Graham et al. |
| 5,290,246 A | 3/1994 | Yamamoto et al. |
| 5,295,969 A | 3/1994 | Fischell et al. |
| 5,330,435 A | 7/1994 | Vaillancourt |
| 5,350,363 A | 9/1994 | Goode et al. |
| 5,352,205 A | 10/1994 | Dales et al. |
| 5,405,323 A | 4/1995 | Rogers et al. |
| 5,456,675 A | 10/1995 | Wolbring et al. |
| 5,487,728 A | 1/1996 | Vaillancourt |
| 5,520,666 A | 5/1996 | Choudhury et al. |
| 5,549,566 A | 8/1996 | Elias et al. |
| 5,549,577 A | 8/1996 | Siegel et al. |
| 5,575,769 A | 11/1996 | Vaillancourt |
| 5,613,663 A | 3/1997 | Schmidt et al. |
| 5,651,772 A | 7/1997 | Arnett |
| 5,657,963 A | 8/1997 | Hinchliffe et al. |
| 5,697,915 A | 12/1997 | Lynn |
| 5,738,144 A | 4/1998 | Rogers |
| 5,749,861 A | 5/1998 | Guala et al. |
| 5,806,831 A | 9/1998 | Paradis |
| 5,817,069 A | 10/1998 | Arnett |
| 5,911,710 A | 6/1999 | Barry et al. |
| 5,954,698 A | 9/1999 | Pike |
| 5,967,490 A | 10/1999 | Pike |
| 6,039,302 A | 3/2000 | Cote, Sr. et al. |
| 6,077,244 A | 6/2000 | Botich et al. |
| 6,117,108 A | 9/2000 | Woehr et al. |
| 6,171,287 B1 | 1/2001 | Lynn et al. |
| 6,273,869 B1 | 8/2001 | Vaillancourt |
| 6,485,473 B1 | 11/2002 | Lynn |
| 6,575,960 B2 | 6/2003 | Becker et al. |
| 6,595,981 B2 | 7/2003 | Huet |
| 6,699,221 B2 | 3/2004 | Vaillancourt |
| 6,719,726 B2 * | 4/2004 | Meng et al. ............... 604/164.07 |
| 6,740,063 B2 | 5/2004 | Lynn |
| 6,883,778 B1 | 4/2005 | Newton et al. |
| 7,008,404 B2 | 3/2006 | Nakajima |
| 7,347,839 B2 | 3/2008 | Hiejima |
| 7,396,346 B2 | 7/2008 | Nakajima |
| 7,470,254 B2 | 12/2008 | Basta et al. |
| 7,736,339 B2 | 6/2010 | Woehr et al. |
| 7,914,494 B2 | 3/2011 | Hiejima |
| 8,357,119 B2 | 1/2013 | Stout et al. |
| 8,361,020 B2 | 1/2013 | Stout |
| 8,388,583 B2 | 3/2013 | Stout et al. |
| 2002/0128604 A1 * | 9/2002 | Nakajima ................ 604/164.01 |
| 2006/0163515 A1 | 7/2006 | Ruschke |
| 2007/0083157 A1 | 4/2007 | Belley et al. |
| 2007/0083162 A1 | 4/2007 | O'Reagan et al. |
| 2007/0233007 A1 | 10/2007 | Adams |
| 2008/0039796 A1 | 2/2008 | Nakajima |
| 2008/0108944 A1 | 5/2008 | Woehr et al. |
| 2010/0204675 A1 | 8/2010 | Woehr et al. |
| 2010/0222746 A1 | 9/2010 | Burkholz |

FOREIGN PATENT DOCUMENTS

| | | |
|---|---|---|
| EP | 0 875 262 A2 | 11/1998 |
| EP | 1 240 916 A1 | 9/2002 |
| EP | 1 679 043 A1 | 7/2006 |
| WO | WO 99/34849 | 7/1999 |
| WO | 2008/052790 A2 | 5/2008 |
| WO | 2009/114833 A1 | 9/2009 |
| WO | 2010/093791 A1 | 8/2010 |

* cited by examiner

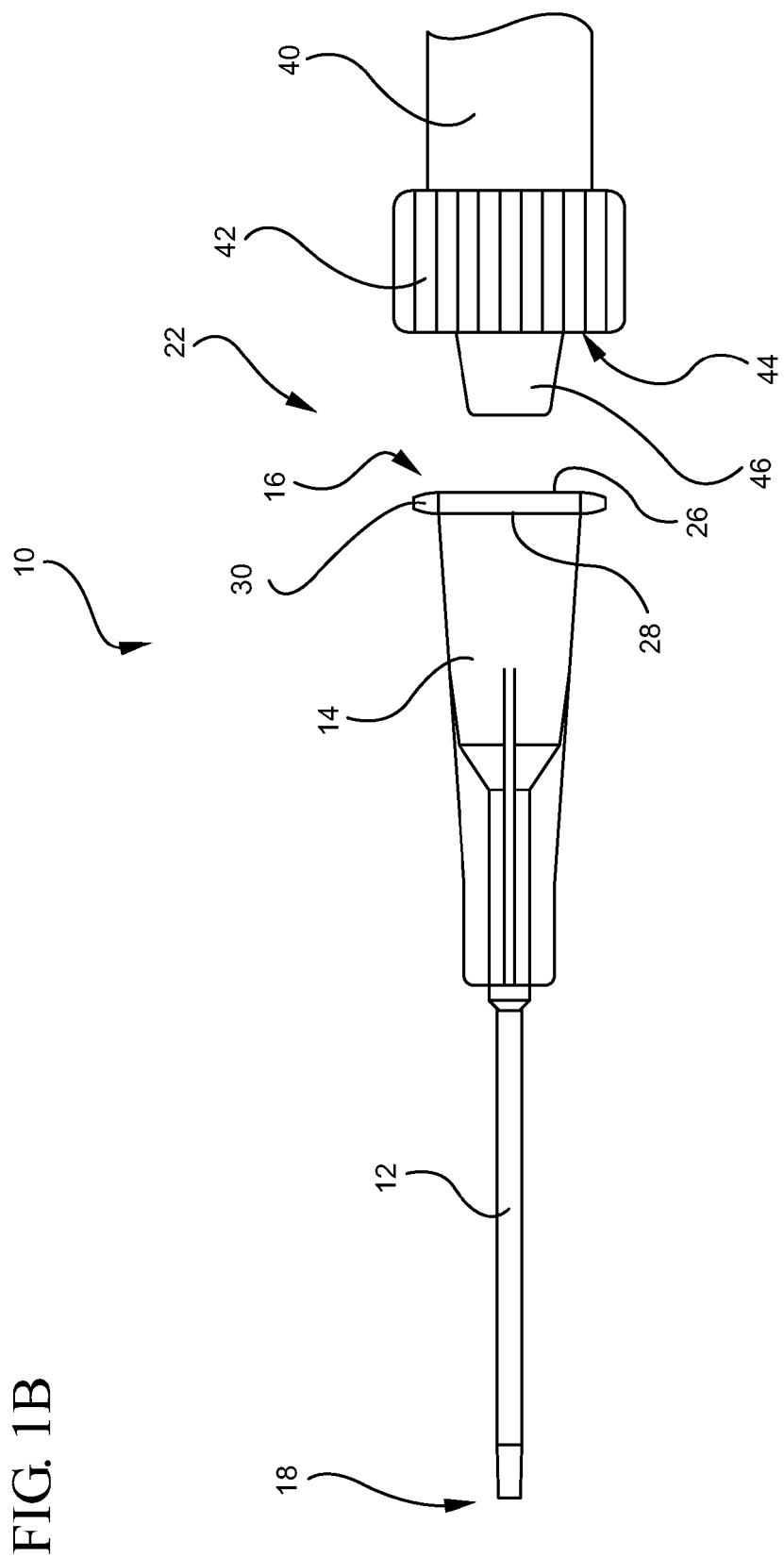

CATHETER ASSEMBLY

BACKGROUND OF THE INVENTION

The current invention relates to infusion devices, specifically to peripheral intravenous (IV) catheters. In particular, the invention relates to a peripheral IV catheter assembly having blood containment features.

Catheters are commonly used for a variety of infusion therapies. For example, catheters are used for infusing fluids, such as normal saline solution, various medicaments, and total parenteral nutrition, into a patient, withdrawing blood from a patient, or monitoring various parameters of the patient's vascular system.

Catheters and/or needles are typically coupled to a catheter adapter to enable attachment of IV tubing to the catheter. Thus, following placement of the catheter or needle into the vasculature of a patient, the catheter adapter is coupled to a fluid source via a section of IV tubing. In order to verify proper placement of the needle and/or catheter in the blood vessel, the clinician generally confirms that there is "flashback" of blood in a flashback chamber of the catheter assembly.

Once proper placement of the catheter is confirmed, the clinician must then attach the catheter adapter to a section of IV tubing, or continue to manually occlude the vein to prevent undesirable exposure to blood. The process of coupling the catheter adapter to the section of IV tubing requires the clinician to awkwardly maintain pressure on the vein of the patient while simultaneously coupling the catheter adapter and the IV tubing. A common, yet undesirable practice is to permit blood to temporarily and freely flow from the catheter adapter while the clinician locates and couples the IV tubing to the catheter adapter. Another common practice is to attach the catheter adapter to the IV tubing prior to placing the needle or catheter into the vein of the patient. While this method may prevent undesirable exposure to blood, positive pressure within the IV line may also prevent desirable flashback.

Accordingly, there is a need in the art for a catheter assembly that permits desirable flashback without the risk of encountering undesirable exposure to blood. Such a catheter assembly is disclosed herein.

BRIEF SUMMARY OF THE INVENTION

In order to overcome the limitations discussed above, the present invention relates to a flushable peripheral IV catheter assembly having blood containment features. The catheter assembly of the present invention generally includes a catheter coupled to a catheter adapter. The catheter may generally include a polymeric catheter in combination with a rigid introducer needle, as is commonly known and used in the art. In some embodiments, the distal portion introducer needle includes a notch to facilitate flashback. The distance between the distal end of the introducer needle and the notch defines a notch distance.

In some embodiments of the present invention, a septum is positioned within a lumen of the catheter assembly to prevent or limit flow of a fluid through the catheter adapter. The septum generally includes a flexible or semi-flexible material that is compatible with exposure to blood, medicaments, and other fluids commonly encountered during infusion procedures. In some embodiments, a groove is provided on an inner surface of the catheter adapter, wherein the septum is seated within the groove. As such, the position of the septum within the catheter adapter is maintained.

A closed or partially closed pathway, such as a slit or small hole is further provided in a barrier surface of the septum. The pathway permits fluid to bypass the septum and flow though the catheter adapter. In some embodiments, the pathway is a slit that is closed prior to being opened or activated by a probe or septum activator positioned within the lumen of the catheter adapter. Prior to being opened or activated, the slit prevents passage of fluid through the catheter adapter.

The septum activator generally includes a plastic, metallic, or elastomeric tubular body having a probing end and a contact end. The probing end is positioned adjacent to the septum, and the contact end is positioned adjacent to a proximal opening of the catheter adapter. The probing end of the septum activator is advanced through the pathway of the septum when a probe is inserted into the proximal opening of the catheter adapter. As the probe contacts the contact surface of the septum activator, the septum activator is advanced in a distal direction through the catheter adapter whereupon the probing end of the septum activator opens the pathway in the septum. Once opened, free flow of fluid is enabled through the catheter assembly.

Finally, the presence of an internal cavity within the septum activator allows blood for blood containment in the case that blood flows across the septum between the distal end of the introducer needle and the needle notch as the introducer needle is being withdrawn. In some embodiments, the internal cavity of the septum activator is in contact with the proximal side of the septum to create an enclosed internal cavity which contains the blood introduced into the internal cavity through the needle notch. In some embodiments, the internal cavity has a length greater than or equal to the notch distance.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 1B is a perspective view of a catheter assembly in accordance with a representative embodiment.

DETAILED DESCRIPTION OF THE INVENTION

The embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

As used herein the term "relief" includes an inward void in a surface. Non-limiting examples of a relief include a channel, a groove, a detent, a slot, a hole, or a notch.

Figure 1A:
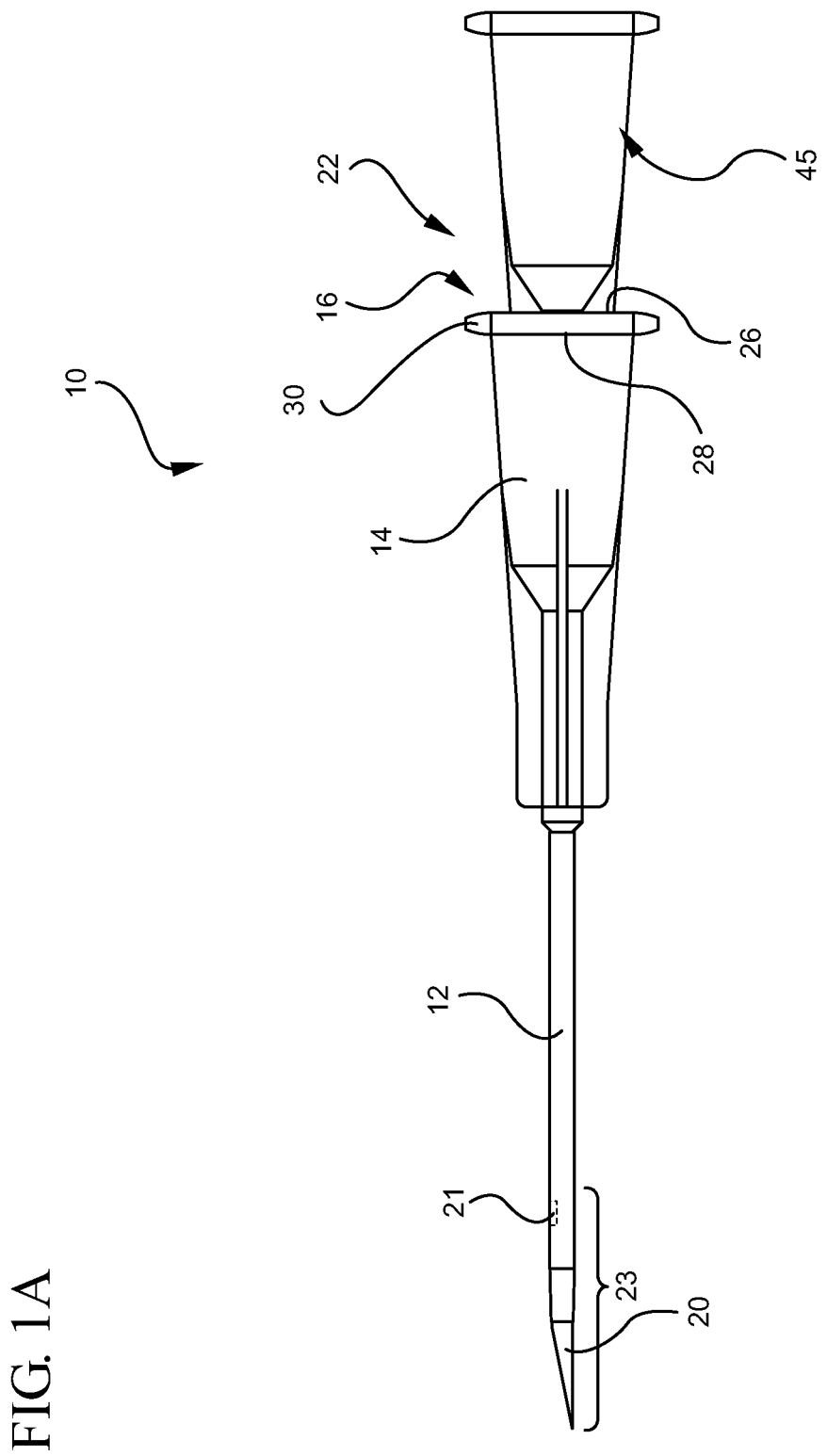
FIG. 1A is a perspective view of a catheter assembly in accordance with a representative embodiment.

Referring now to FIG. 1A, a catheter assembly 10 is illustrated. The catheter assembly 10 generally includes an over-the-needle catheter 12 coupled to a distal end of a catheter adapter 14. The catheter 12 is disposed over an introducer needle 20 when in a pre-use position. In order to verify proper placement of the needle 20 and the catheter 12 in the blood vessel, the clinician generally confirms that there is blood flashback through the catheter assembly 10. Thereafter, the introducer needle 20 is removed from within the catheter 12 after the catheter and introducer needle 20 are inserted into the vasculature of a patient.

Flashback confirmation is facilitated by a needle notch 21 in the distal portion of the introducer needle 20. Because the needle notch is on a portion of the needle that is within the catheter, an outline of the needle notch is shown in dashed lines. The distance between the proximal end of the notch 21 and the distal tip of the needle is herein referred to as a "notch distance" 23. When properly placed in the vasculature of a patient, blood flows through the introducer needle 20 and out the needle notch 21. In some embodiments, there is a space between the interior surface of catheter 12 and the exterior surface of the introducer needle 20 through which blood flows during flashback toward the catheter adapter 14. After flashback is confirmed, a clinician may withdraw the introducer needle 20 from the catheter 12, leaving the catheter within the patient.

Once inserted into a patient, the catheter 12 and catheter adapter 14 provide a fluid conduit to facilitate delivery of a fluid to and/or retrieval of a fluid from a patient, as required by a desired infusion procedure. Thus, the material of the catheter 12 and the catheter adapter 14 are selected to be compatible with bio-fluids and medicaments commonly used in infusion procedures. Additionally, in some embodiments a portion of the catheter 12 and/or catheter adapter 14 is configured for use in conjunction with a section of intravenous tubing 40 to further facilitate delivery of a fluid to or removal of a fluid from a patient.

In some embodiments, a proximal end 22 of the catheter adapter 14 includes a flange 28. The flange 28 provides a positive surface which may be configured to enable coupling of an intravenous tubing or patient conduit 40 to the catheter assembly 10. In some embodiments, a needle hub 45 of the introducer needle 20 is coupled to the flange prior to removal of the needle from the catheter.

Referring now to FIG. 1B, after the removal of the needle hub 45 from the proximal end of the catheter adapter 14, the catheter assembly may be coupled to a separate vascular access device, such as a conduit coupler 42. In some embodiments, the flange 28 includes a connector 30 for receiving a separate vascular access device. The connector 30 is generally provided and configured to compatibly receive a complementary connector 44 comprising a portion of a male luer or conduit coupler 42. The conduit coupler 42 is generally coupled to an end portion of the patient conduit 40 in a fluid-tight manner. In some embodiments, an inner portion of the conduit coupler 42 is extended outwardly to provide a probe surface 46.

Figure 5:
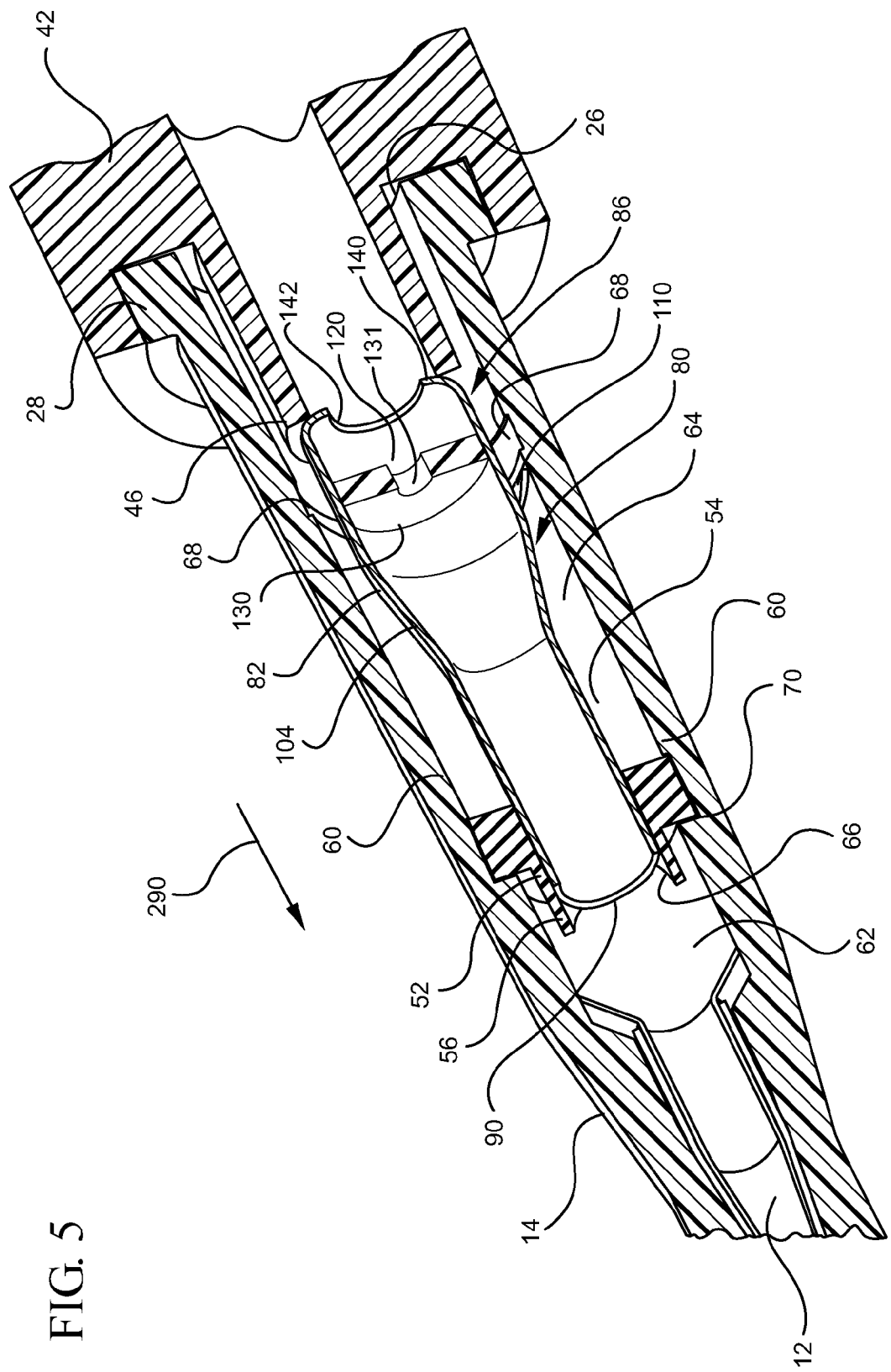
FIG. 5 is a cross-sectional view of an assembled catheter assembly in accordance a representative embodiment, following activation.

The probe surface 46 is generally configured to compatibly insert within a proximal end 22 of the catheter adapter 14. Following insertion of the probe 46 into the proximal end 22 of the catheter adapter 14, the conduit coupler 42 is rotated to interlock the coupler 42 and the flange 28 (via the sets of threads 30 and 44). During the process of interlocking the coupler 42 and the flange 28, the probe 46 is advanced into the lumen 16 of the catheter adapter 14 to an inserted position (as shown in FIG. 5). The inserted position of the probe surface 46 activates the catheter assembly 10 to enable flow of fluid through the catheter 12 and catheter adapter 14. Once the conduit coupler 42 and the catheter adapter 14 are attached, a fluid may be delivered to a patient via the patient conduit 40 and the inserted catheter 12.

Figure 2A:
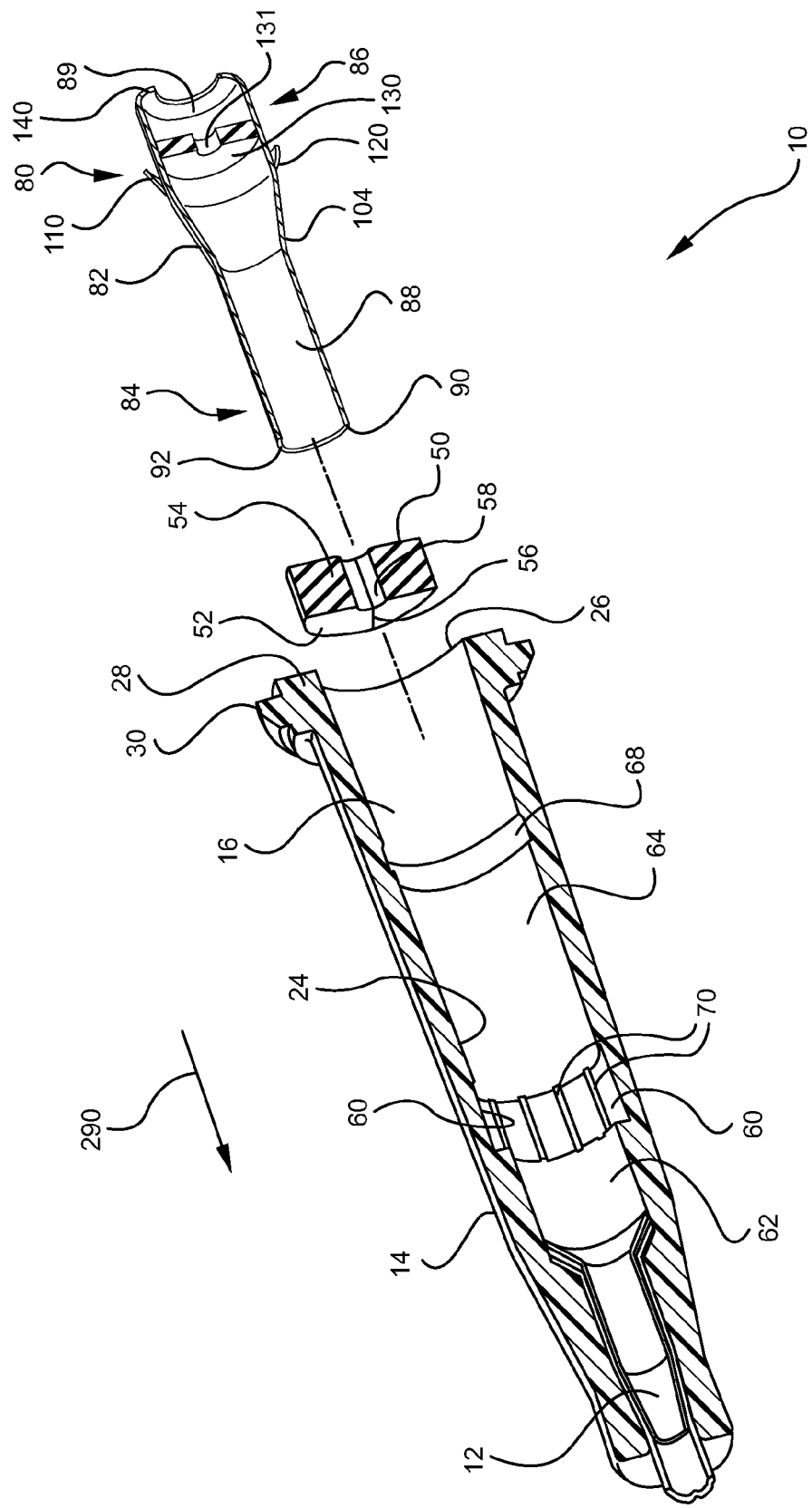
FIG. 2A is an exploded cross-sectional view of a catheter assembly in accordance with a representative embodiment.

Referring now to FIG. 2A, an exploded, cross-sectional view of a catheter assembly 10 is shown. In some embodiments, the catheter adapter 14 includes various design features and components to control and/or limit flow of fluid through the catheter assembly 10. For example, in some embodiments of the present invention a septum 50 is positioned within the inner lumen 16 of the catheter adapter 14. The septum 50 generally comprises a flexible or semi-flexible polymer plug having an outer diameter that is configured to compatibly seat within a groove or channel 60 formed on an inner surface 24 of the catheter adapter 14. In some embodiments, the septum 50 is disk shaped having a distal and a proximal surface. When positioned within the channel 60, the barrier surface (the distal surface) 52 of the septum 50 divides the inner lumen 16 of the catheter adapter 14 into a forward fluid chamber 62 and a rearward fluid chamber 64. Thus, the presence of the septum 50 controls or limits passage of fluid between the forward and rearward fluid chambers 62 and 64. Specifically, a chosen configuration of the barrier surface 52 of the septum 50 largely determines the ability of a fluid to flow through the inner lumen 16 of the catheter adapter 14.

For example, in some embodiments the barrier surface 52 of the septum 50 is configured to include a slit 56. The slit 56 is configured to provide selective access or flow of a fluid through the barrier surface 52. In some embodiments, the slit 56 is configured to remain in a closed, fluid-tight position until activated or opened by advancing a septum activator 80 through the slit 56 in a distal direction 290. In some embodiments, the barrier surface 52 comprises one slit 56. In other embodiments, the barrier surface 52 is modified to include multiple slits.

For some infusion therapy techniques, it may be desirable to permit a controlled flow of fluid through the septum 50 prior to activating the septum 50 with the septum activator 80. Thus, in some embodiments the slit 56 further comprises a leak orifice 58. The leak orifice 58 is positioned in the barrier surface 52 and comprises an opening diameter calculated to permit controlled flow of liquid or air between the forward and rearward chambers 62 and 64. In some embodiments, the barrier surface 52 is modified to include a single leak orifice 58. In other embodiments, the barrier surface 52 is configured to include multiple leak orifices. Still, in other embodiments the barrier surface 52 does not include a slit 56, but rather includes at least one leak orifice 58. For these embodiments, the septum 50 generally comprises an elastic material such that when the septum activator 80 is advanced in a distal direction 290, a leading edge 92 of the septum activator 80 contacts the barrier surface 52 and stretches the leak orifice 58 to provide a larger orifice, thereby permitting increased flow of air and/or fluid through the catheter adapter 14.

The groove or channel 60 into which the septum is seated comprises a recessed portion of the inner surface 24 of the catheter adapter 14. The outer diameter of the septum 50 is generally configured to compatibly and securely seat within the channel 60. For example, in some embodiments the outer diameter of the septum 50 is selected to be both slightly smaller than the diameter of the channel 60 and slightly larger than the diameter of the inner lumen 16. As such, the septum 50 is retained within the channel 60 during use of the catheter assembly 10.

For some infusion therapy techniques, air flow between the forward and rearward chambers 62 and 64 may be desirable. For example, for those embodiments comprising a septum 50 having a fluid-tight slit 56, passage of air from the forward chamber 62 to the rearward chamber 64 is prohibited prior to opening or activating the septum 50 via the septum activator 80, as previously discussed. Thus, when the catheter 12 of the catheter assembly 10 is inserted into the vascular system of a patient, a positive pressure develops within the forward chamber 62 thereby preventing a desired flashback of the patient's blood into the catheter adapter 14. An observable flashback is generally desirable to confirm accurate placement of the catheter tip within the vein of the patient. Thus, some embodiments of the present invention include features or elements to enable airflow between the forward chamber 62 and the rearward chamber 64, without requiring activation of the septum 50 with the septum activator 80. As such, some embodiments of the present invention provide an observable flashback, as generally desired for infusion procedures.

For example, in some embodiments the barrier surface 52 of the septum 50 is modified to include leak orifice 58, as previously discussed. In other embodiments, a plurality of air vent channels 70 is interposed between the septum 50 and the inner surface 24 of the catheter adapter 14. The air vent channels 70 relieve the positive pressure within the forward chamber 62 by providing an access for air to bypass the septum 50 into the rearward chamber 64. In some embodiments, the air vent channels 70 are constructed by removing portions of the channel 60 surface, resulting in a plurality of generally parallel grooves.

In addition to permitting air flow between the forward and rearward chambers 62 and 64, the vent channels 70 may be configured to permit fluid to flow through the catheter adapter 14 prior to activating or opening the slit 56 with the septum activator 80. In some embodiments, the rate at which air and/or fluid flows between the forward and rearward chambers 62 and 64 is adjusted by manufacturing the catheter adapter 14 to include a greater or lesser number of vent channels 70. In other embodiments, the rate at which air and/or fluid flows between the forward and rearward chambers 62 and 64 is adjusted by manufacturing the catheter adapter 14 to include vent channels 70 having a greater or lesser cross-sectioned area. Thus, in some embodiments the rate at which air and/or fluid flows between the forward and rearward chambers 62 and 64 is increased by manufacturing a catheter adapter 14 having either an increased number of vent channels 70, or vent channels 70 having a greater cross-sectioned area. Conversely, in other embodiments the rate at which air and/or fluid flows between the forward and rearward chambers 62 and 64 is decreased by manufacturing a catheter adapter 14 having either a decreased number of vent channels 70, or vent channels 70 having a lesser cross-sectioned area.

With continued reference to FIG. 2A, the septum activator 80 comprises a probe-like structure that is primarily housed in the rearward chamber 64 of the catheter adapter 14. The septum activator 80 generally comprises a body 82 having a distal end 84 and a proximal end 86. The body 82 comprises a rigid or semi-rigid material, such as a plastic, metallic, or elastomeric material. The body 82 further comprises an internal cavity 88, which in some embodiments opens at the distal end. In some embodiments, the internal cavity 88 has an inner volume greater than the volume of a portion of the introducer needle 20, which resides therein prior to the removal of the needle from the catheter adapter 14. In some embodiments, the internal cavity 88 includes an inner diameter greater than the outer diameter of the introducer needle 20. In some embodiments, the internal cavity 88 includes an inner diameter substantially greater than the outer diameter of the introducer needle 20.

Figure 7:
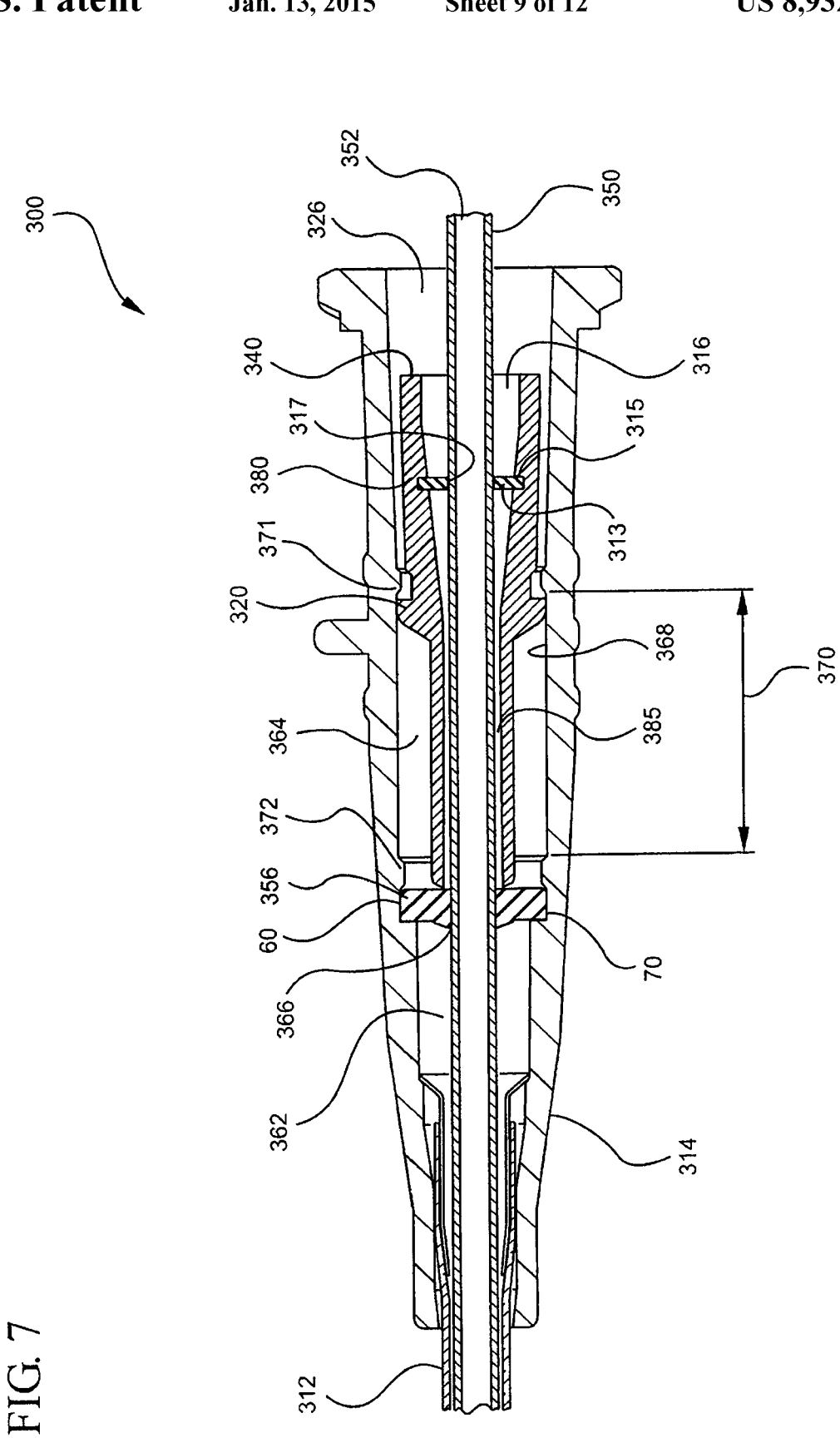
FIG. 7 is a cross-sectional view of an assembled over-the-needle catheter assembly in accordance a representative embodiment, prior to activation.

The internal cavity 88 comprises a cavity seal 130 positioned within the body 82. The cavity seal 130 forms a proximal portion 89 of the internal cavity 88. In some embodiments, the cavity seal 130 is a proximal wall surface of the internal cavity 88. In some embodiments, the cavity seal 130 of the internal cavity 88 is integrated into the body of the septum activator 80. In other embodiments, the cavity seal 130 is a separate component, which is inserted within a groove in the septum activator, as shown in FIG. 7. The cavity seal includes a hole 131, which, in some embodiments, has a diameter equal to or greater than the diameter of the introducer needle 20. However, in other embodiments, the hole is slightly smaller than the diameter of the introducer needle 20 in order to provide a fluid tight seal between the introducer needle 20 and the cavity seal 131. During catheter placement and introducer needle removal, the introducer needle 20 extends through the hole 131 of the cavity seal. When inside the hole, the introducer needle 20 seals or substantially seals the internal cavity 88 to prevent fluid from exiting the hole 131.

Figure 4:
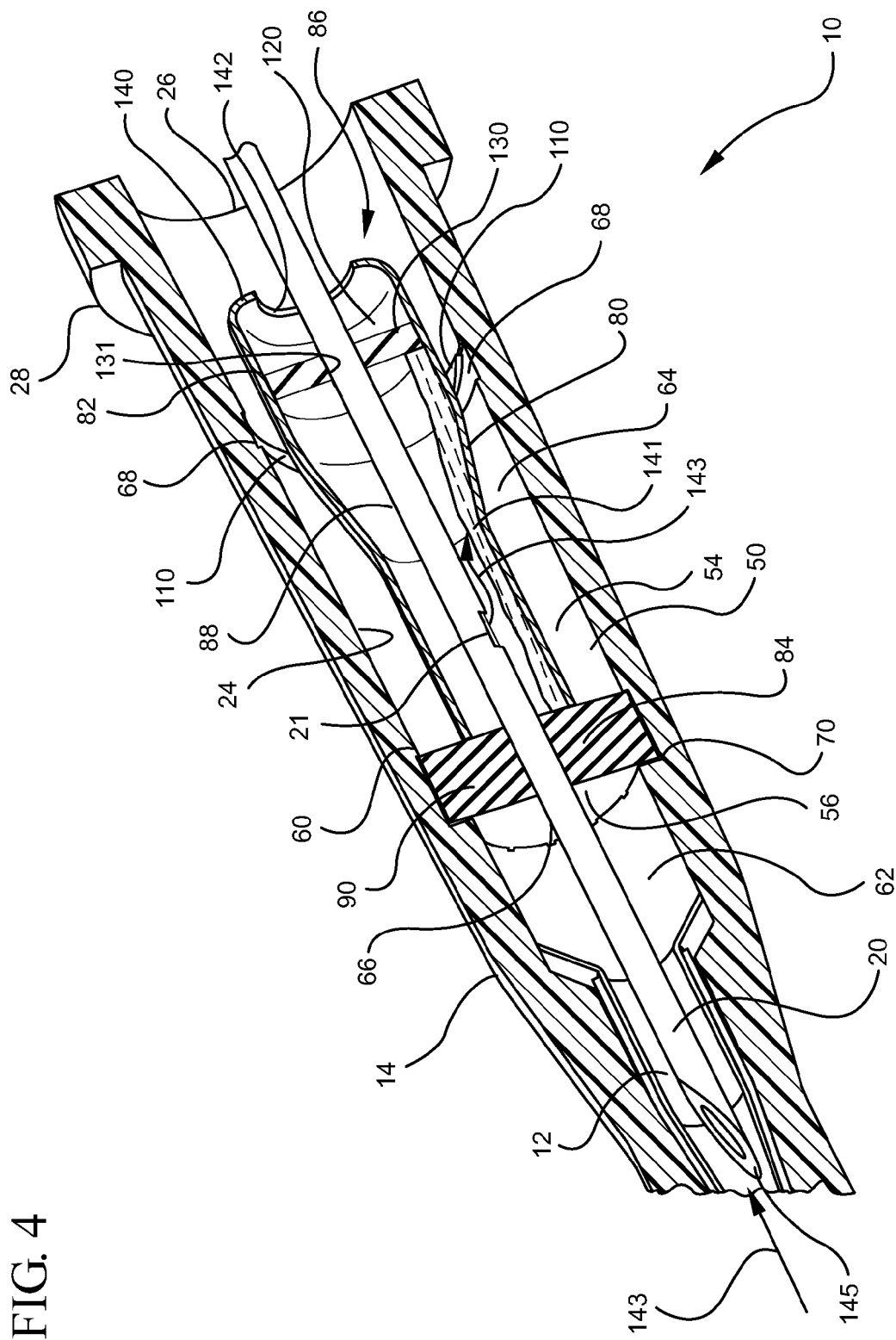
FIG. 4 is a cross-sectional view of an assembled catheter assembly in accordance with a representative embodiment, prior to activation.

The distal end 84 of the tubular body 82 is configured to compatibly insert through the septum 50. Prior to insertion, a probing surface 90 on the distal end 84 is adjacent to the proximal surface of the septum 50 in order to enclose or substantially enclose the internal cavity 130 of the septum activator 80. In some embodiments, substantially the entire probing surface contacts the proximal surface of the septum 50. In this way, blood flowing through the septum 50 is contained within the internal cavity 130 and does not escape between the probing surface 90 of the septum activator 80 and the septum. During septum activation, the probing surface 90 is advanced in a distal direction through the slit 56 and 66, or through the leak orifice 58, as shown in FIGS. 4-5.

In some embodiments the septum 50 is coated with a hydrophobic coating, or a polymeric swelling coating to repel or prevent fluid from flowing through the vent channels 70. A hydrophobic coating is generally selected to reduce the surface energy of the septum 50 and/or adapter 14 to inhibit blood wicking into the air vents 70. In some embodiments, a surface of the septum 50 or catheter adapter 14 is coated with a polyxylylene polymer material, such as parylene. Parylene is a chemically resistant coating with good barrier properties for inorganic and organic fluids, strong acids, caustic solutions, gases and water vapors. In some embodiments, a parylene coating is applied to the outer surface of the septum 50 via vapor deposition. In other embodiments, a polyxylylene polymer coating is applied to a vent channel 70 via vapor deposition.

In some embodiments, a dehydrated polymer material is applied to a surface of the septum 50 or catheter adapter 14 which comprises the vent channels 70. A dehydrated polymer is generally selected to expand or swell upon contact with fluid. As such, when the dehydrated polymer swells, a flow through the vent channels 70 is blocked or occluded by the swollen polymer. Initially, the dehydrated polymer generally comprises a thin profile prior to exposure to moisture. However, when exposed to moisture the polymer absorbs the moisture which increases the profile of the polymer to block flow through the vent 70. Therefore, by coating the septum 50 and/or catheter adapter 14 with a desired coating, flow of air is permitted between the forward and rearward chambers 62 and 64, yet fluid flow through the vent channels 70 is prevented.

Figure 2B:
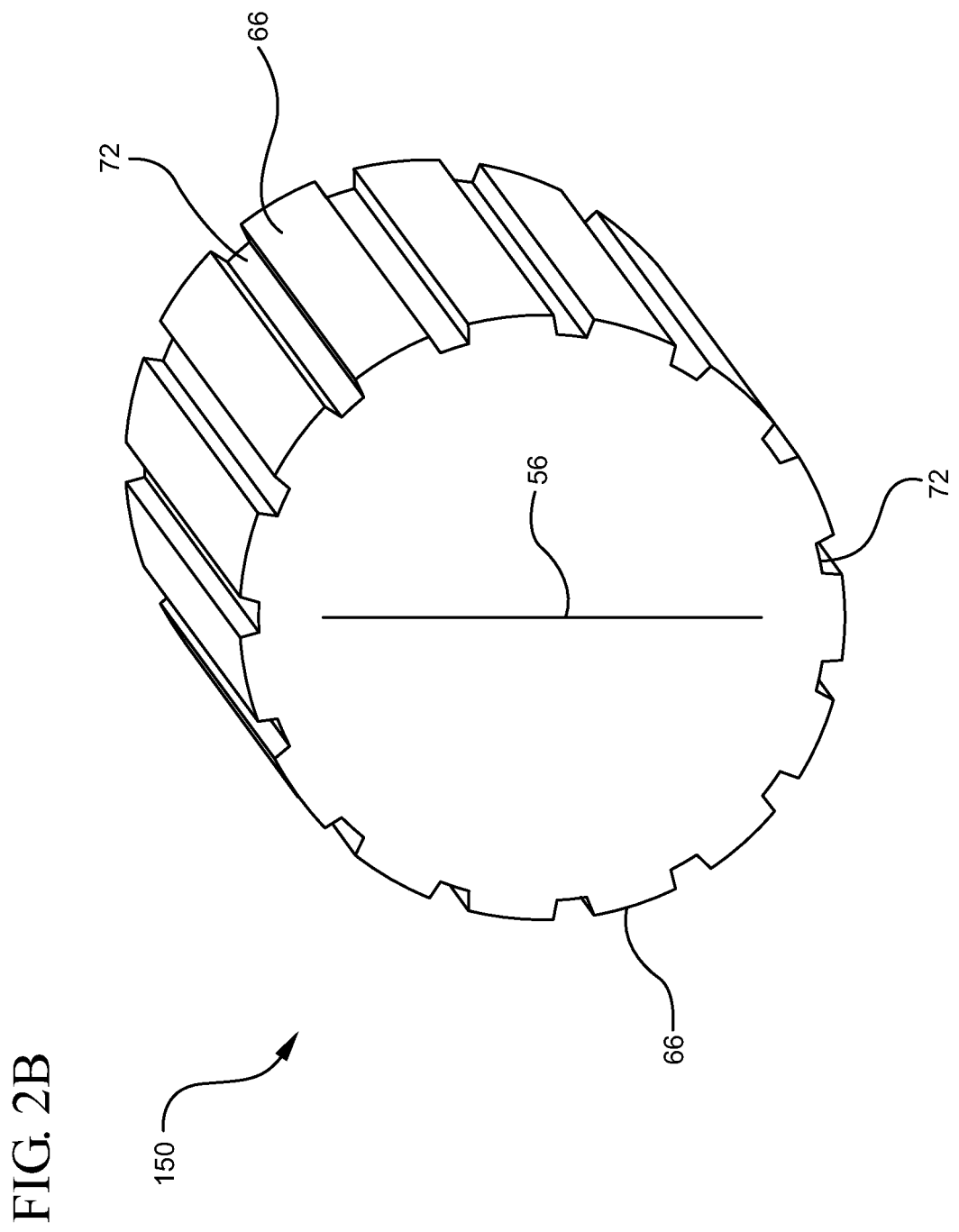
FIG. 2B is a perspective view of a septum in accordance with a representative embodiment.

Referring now to FIG. 2B, an embodiment of a septum 150 is shown. In some embodiments, an outer surface 66 of the septum 150 is modified to include a plurality of recessed grooves 72. The recessed grooves 72 provide pathways between the forward and rearward chambers 62 and 64 through which air and/or fluid may flow. Thus, in some embodiments the channel 60 does not include air vent channels 70, but rather the outer surface 66 of the septum 150 is modified to provide desired flow between the forward and rearward chambers 62 and 64.

Figure 3:
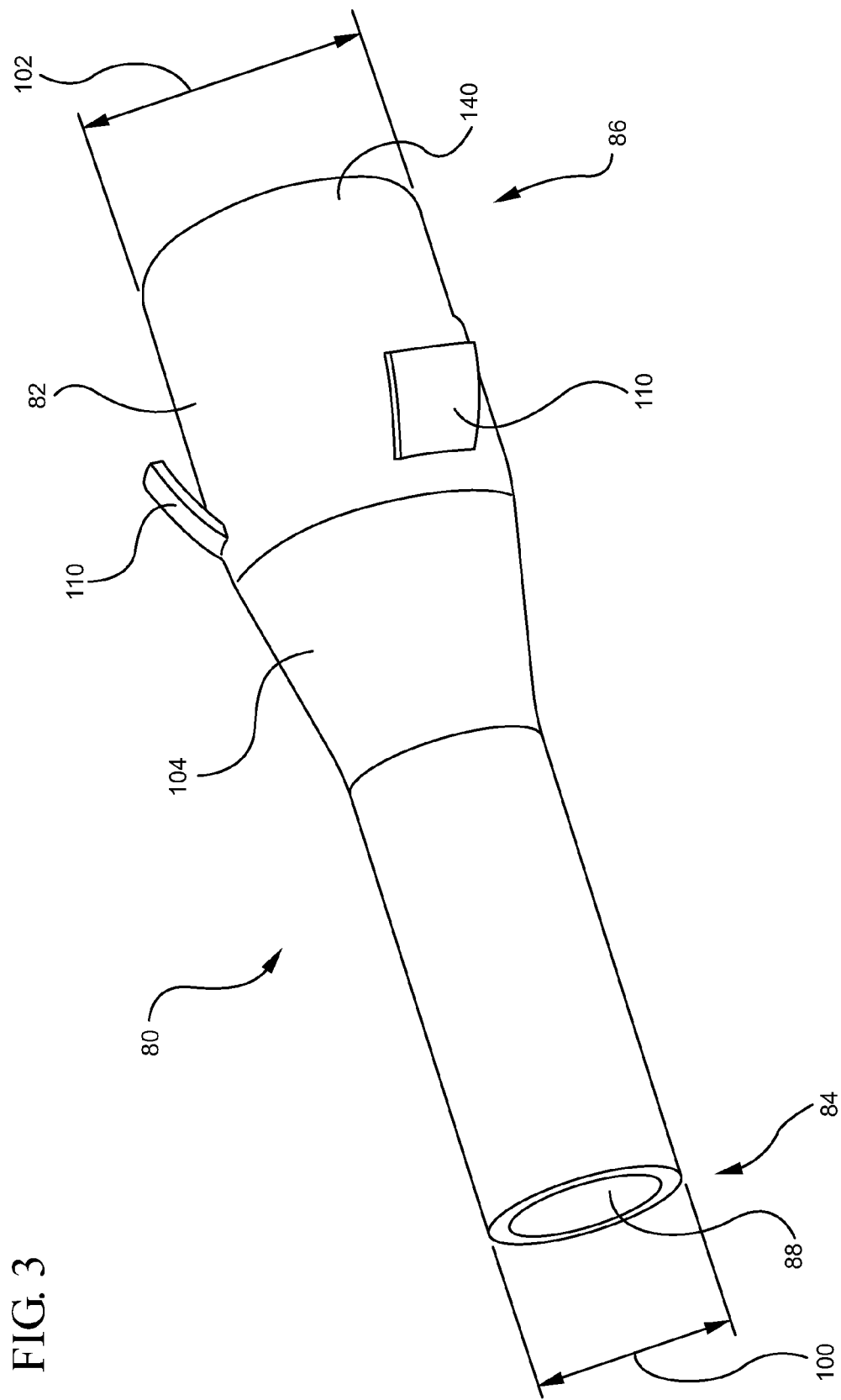
FIG. 3 is a perspective view of a septum activator in accordance with a representative embodiment.

Referring now to FIG. 3, a perspective view of the septum activator 80 is shown. In some embodiments, the distal end 84 of the tubular body 82 comprises a first diameter 100 that is less than a second diameter 102 of the proximal end 86. The narrower distal end 84 is configured to compatibly insert within the opening 54 of the septum 50, while the wider proximal end 86 is configured to compatibly seat within the rearward chamber 64 of the catheter adapter 14. In some embodiments, the septum activator further includes a tapered middle section 104 to couple the distal 84 and proximal 86 ends. In other embodiments, distal and proximal ends of the septum activator comprise substantially the same diameter.

In some embodiments, the proximal end 86 of the septum activator 80 further includes a retention spring 110. The retention spring 110 generally comprises an outwardly biased portion of the tubular body 82 configured to compatibly engage a septum activator retention groove 68, as shown in FIGS. 2A, and 4-5. The interaction between the retention spring 110 and the groove 68 limits the lateral movement of the septum activator 80 within the lumen 16 of the catheter adapter 14. Thus, the width of the retention groove 68 determines or limits the distance of travel for the septum activator 80 within the catheter adapter 14. Additionally, the interaction between retention spring 110 and the groove 68 prevents removal of the septum activator 80 from the catheter adapter 14 and maintains the probing surface 90 of the septum activator in contact with the septum. In some embodiments, the septum activator 80 comprises a plurality of retention springs 110, while in other embodiments the septum activator 80 comprises a single retention spring 110. In some embodiments, the retention groove 68 is replaced with another relief structure, such as a channel, a detent, a slot, a hole, or a notch. In other embodiments, the location of the retention spring 110 and the relief structure is reversed, such that the retention spring is disposed on the inner surface of the lumen 16 of the catheter adapter 14 and the relief structure is disposed on the septum activator 80.

The proximal end 86 of the septum activator 80 further includes a contact surface 140. The contact surface 140 comprises the most proximal end portion of the septum activator 80 and is positioned within the rearward chamber 64 of the catheter adapter 14 adjacent to the proximal opening 26 of the catheter adapter 14, as shown in FIG. 4, below.

Referring now to FIG. 4, a cross-sectional view of the assembled catheter assembly 10 is shown prior to activation of the septum 50 via the septum activator 80 and during removal of the introducer needle 20. Prior to activation, the septum activator 80 is entirely positioned within the rearward fluid chamber 64 of the catheter adapter 14. Additionally, the retention springs 110 are engaged within the retention groove 68 and positioned near the proximal end of the retention groove 68. The contact surface 140 of the septum activator 80 is positioned near the opening 26 of the catheter adapter 14, such that a proximal opening 142 of the septum activator 80 is in a plane generally parallel to the plane of the catheter adapter opening 26. Finally, the outwardly biased retention springs 110 bind on the surface of the groove 68 thereby maintaining the inactivated position of the septum activator 80 within the catheter adapter 14.

In some embodiments, the retention springs 110 additionally serve to maintain the probing surface 90 of the septum activator 80 in contact with the proximal side of the septum 50. The septum generally includes a flat proximal surface that closes and/or seals the distal opening of the internal cavity 88 of the septum activator 80. As such, the internal cavity 88 is substantially enclosed prior to septum activation. During removal of the introducer needle 20, the needle is drawn proximally out the catheter 12 and the catheter adapter 14. At certain points during removal, the tip 145 of the introducer needle is distal the septum 50 while the needle notch 21 is proximal the septum 50. At these times, blood 141 flowing from the patient through the catheter 12 may enter the tip 15 of the introducer needle 20 and exit through the needle notch, thus defeating the septum 50. This fluid path 143 is illustrated in FIG. 4.

Absent the internal cavity 88 of the septum activator, blood flowing through the fluid path 143 would enter the rearward chamber 64 and potentially exit through the proximal opening 26 of the catheter adapter 14. To prevent this blood exposure, the septum activator includes the internal cavity 88, which, in some embodiments, is substantially enclosed to receive the blood 141 and prevent blood exposure through the proximal end 26 of the catheter assembly 14. Accordingly, in some embodiments, the length of the internal cavity 88 is greater than or equal to the needle notch distance 23 to prevent both the septum 50 and the internal cavity 88 from being defeated. After septum activation, fluid flows through the internal cavity 88 of the septum activator and may flush the blood 141 from the internal cavity 88.

Referring now to FIG. 5, a cross-sectional view of the catheter assembly 10 is shown following activation of the septum 50 via the septum activator 80. Upon insertion of the coupler 42 into the proximal opening 26 of the catheter adapter 14, the probe portion 46 of the coupler 42 contacts the contact surface 140 of the septum activator 80. The septum activator 80 is advanced in a distal direction 290 as the coupler 42 is further inserted into the proximal opening 26 of the catheter adapter 14. As the coupler 42 is advanced further into the proximal opening 26, the probing surface 90 of the septum activator 80 passes through the barrier surface 52 of septum 50. As such, the probing surface 90 of the septum activator 80 is positioned within the forward chamber 62 providing a fluid pathway through the septum 50. In the activated position, fluid can be introduced into the catheter assembly 14. Fluid entering the catheter adapter 14 enters the septum activator 80 and passes through the hole 131 of the cavity seal, through the internal cavity 88, through the catheter 12, and into the patient.

In some embodiments, the catheter assembly 10 is configured to permit the septum activator 80 to return to a position entirely within the rearward chamber 64 following removal of the coupler 42 from the catheter adapter 14. Thus, when the coupler 46 is removed or detached from the catheter assembly 10, the fluid pathway through the septum 50 is reclosed. In some embodiments, the retention spring 110 is configured to flex inwardly upon contact between the contact surface 140 of the septum activator 80 and the probe 46 of the coupler 42. When the retention spring 110 flexes inwardly, the probing surface 90 of the septum activator 80 is temporarily advanced in a distal direction 290 to bias open the slits 66 and 56, or the leak orifice 58. When contact between the probe 46 and the contact surface 140 ceases, the retention spring 110 returns to its relaxed position. The relaxed position withdrawals the probing surface 90 of the septum activator 80 from the barrier surface 52 thereby permitting closure of the slits 66 and 56.

Figure 6:
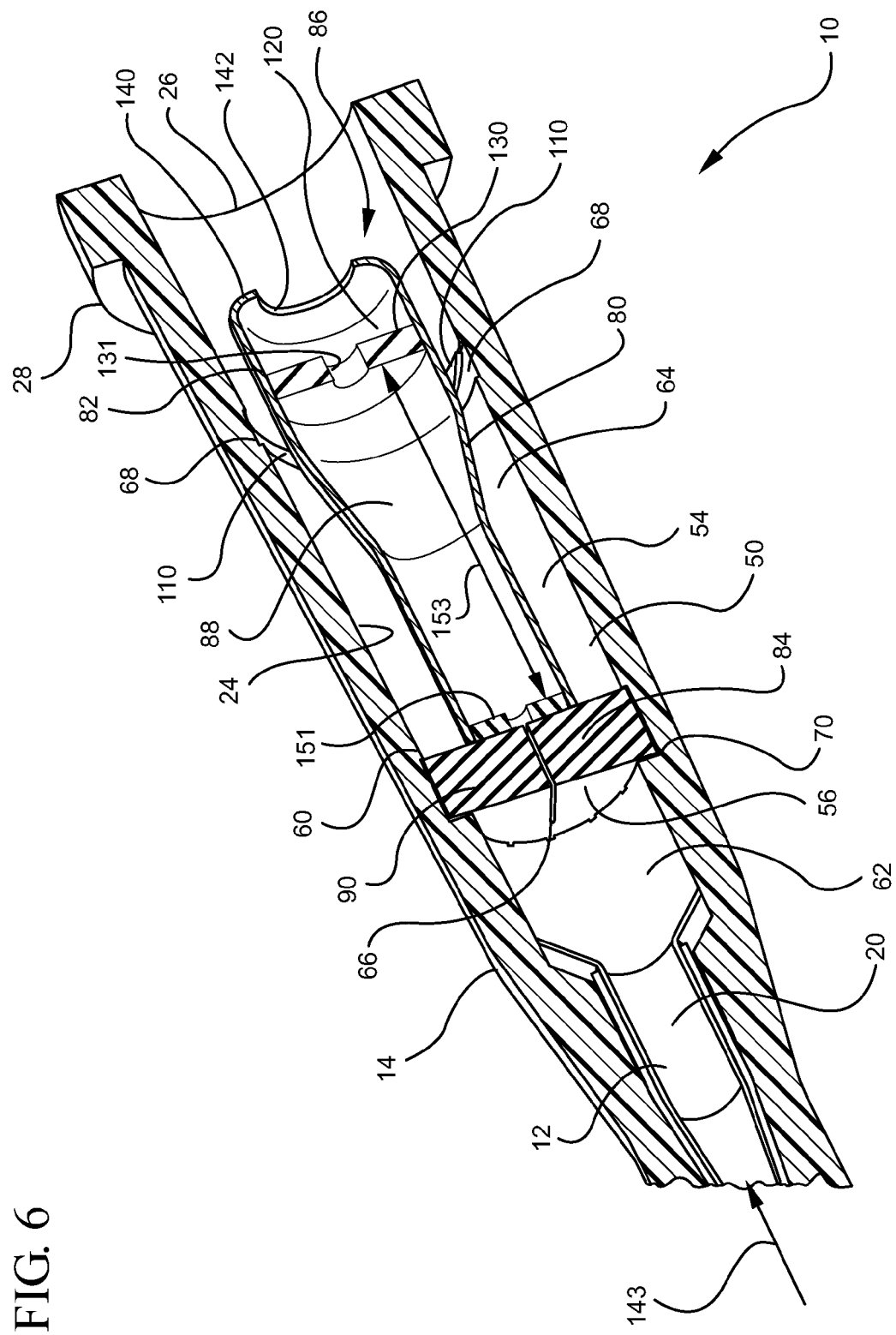
FIG. 6 is a cross-sectional view of an assembled catheter assembly in accordance a representative embodiment, prior to activation.

Referring now to FIG. 6, a cross-sectional view of a catheter assembly 14 is shown, similar to that of FIG. 4. In some embodiments, the internal cavity 88 of the septum activator 80 includes a second or distal cavity seal 151 disposed on the distal end of the internal cavity 88. The second cavity seal 151 substantially encloses the internal cavity 88 to ensure blood containment within the internal cavity 88 despite adjustments of the probing surface 90 of the septum activator 80, which may otherwise result in some blood leakage. The second cavity seal 151 comprises a hole 153 through which the introducer needle 20 is inserted prior to removal, and through which fluid flows during septum activation.

Referring now to FIG. 7, a cross-sectional view of a catheter assembly 300 is shown incorporating an introducer needle 350. One of skill in the art will appreciate that the proximal end 352 of the needle 350 may be coupled to a needle hub (not shown) or an insertion assembly (not shown) to facilitate a user in holding and manipulating the needle 350 during catheterization. For purposes of clarity in the present illustration the remainder of the needle assembly has been removed.

Prior to activation, septum activator 380 is entirely positioned within the rearward chamber 364 of catheter adapter 314. A pathway is provided through the inner lumen 316 of the activator 380 so as to allow passage of introducer needle 350. A middle portion of the needle 350 passes through septum 356 and continues through the forward chamber 362 and into the flexible catheter 312. A tip portion (not shown) of the needle 350 extends beyond a tip portion (not shown) of the catheter 312 such that the needle tip is available to gain access to the vasculature of a patient.

The slit 366 of septum 356 is biased open by the introducer needle 350. In some embodiments, a seal is formed between the outer surface of the needle 350 and the slit 366. Thus, fluid and air flow are prevented from bypassing the septum by way of the interface between the needle 350 and the slit 366. In some embodiments, a channel or pathway is provided between the slit 366 and the needle 350 to permit controlled leakage or flow between these two components.

In other embodiments, a lubricant such as a non-wetting lubricant is applied to the interface between the needle 350 and the slit 366 to further eliminate possible leakage of fluid and/or air. A non-wetting lubricant may also be beneficial to prevent tearing or other damage to the slit that may occur when the needle is removed from the catheter assembly following catheterization. A non-wetting lubricant may also facilitate proper realignment of the slit 366 halves following removal of the needle 350. Non-limiting examples of a non-wetting lubricant include fluorinated silicone oil lubricants, such as NuSil Med 460 non-wetting fluorinated silicone oil; non-fluorinated silicone oils, known Teflon based non-wetting materials such as Endura, from Endura Coating Co.; A20, E-20, 1000-S20, FEP Green, PTFE and X-40 from Tiodize; Cammie 2000 from AE Yale; 21845 from Ladd Research; MS 122-22, MS 122DF, MS-143DF, MS-122V MS-122VM, MS143V, MS-136W, MS-145W, U0316A2, U0316B2, MS-123, MS-125, MS-322 and MS-324 from Miller-Stepheson; and 633T2 from Otto Bock can also be used. Various non-Teflon based non-wetting lubricant type materials include Dylyn, from ART; Nyebar, Diamonex, NiLAD, TIDLN, Kiss-Cote, Titanium oxide; Fluocad Fluorochemical Coating FC-722, from 3M; Permacote from Dupont; Plasma Tech 1633 from Plasma Tech, Inc.; and silicone sprays.

Lubricant can be applied to the septum slit 366 during manufacturing of the catheter assembly. Accordingly, in some implementations, a lubricant is placed on the tip of the introducer needle 350 and/or the tip of the septum activator 380. During manufacture, the lubricated tip of the introducer needle and/or the lubricated tip of the septum activator is inserted through the septum slit 366, which movement transfers the lubricant onto the inner slit surfaces. In some implementations, the needle 350 is inserted into the septum slit 366 first and then followed by the insertion of the septum activator 380. Both the needle and the septum activator 380 can then be removed and made ready for use. In this manner, lubricant can be applied to the septum slit 366.

In some embodiments, two separate lubricants are applied to the septum slit 366. In some embodiments, a first lubricant is applied to the distal end of the introducer needle 350 and thereby applied to the septum slit 366. Next, a second lubricant is applied to the distal end of the septum activator 380 and thereby applied to the septum slit 366.

In some embodiments, distal end 384 of the septum activator 380 is elongated such that contact surface 340 is positioned closer to proximal opening 326 of the catheter adapter 314. Accordingly, a coupler having a shortened probe portion (not shown) may sufficiently contact the contact surface 340 to advance the distal end 384 through the septum 356. In other embodiments, the distal end 384 of the septum activator 380 is shortened to accommodate a longer probe portion.

In some embodiments, a translating groove 368 is provided within the rearward chamber 364. The translating groove 368 generally comprises an annular recess having a determined length 370. Translating groove 368 is further configured to receive flushing fins 320 such that the flushing fins 320 are retained within the groove 368. The translating groove may maintain the distal portion of the septum activator in contact with the septum. Thus, length 370 represents the maximum lateral distance which septum activator 380 is permitted to travel within the rearward chamber 364. In some embodiments, a proximal end of groove 368 is defined by an annular ridge 371. In other embodiments, a distal end of groove 368 is defined by a second annular ridge 372. Still, in other embodiments the second annular ridge 372 forms a proximal end of septum channel 60. In other embodiments, the translating groove 68 is replaced with another relief structure. In some embodiments, the flush fins 320 are replaced with another protruding, retaining feature. In other embodiments, the translating groove 68 disposed on the septum activator 380 and a protruding retaining feature is disposed on the inner surface of the lumen 16 of the catheter adapter 14.

In some embodiments, a seal 315 is positioned within the internal cavity 385 of the septum actuator 380. The cavity seal 315 generally comprises a semi-rigid, semi-flexible, or flexible plug having an outer diameter that is configured to compatibly seat within a groove or channel 313 formed on an inner surface of the septum actuator 380. In some embodiments, the cavity seal 315 comprises an opening 317 near the center of the cavity seal 315. In some embodiments, the groove or channel 313 into which the cavity seal 315 is seated comprises a recessed portion of the inner surface of the septum actuator 380. The outer diameter of the cavity seal 315 is generally configured to compatibly and securely seat within the channel 313. For example, in some embodiments the outer diameter of the cavity seal 315 is selected to be both slightly smaller than the diameter of the channel 60 and slightly larger than the diameter of the inner lumen 16. As such, the cavity seal 315 is retained within the channel 60 during use of the catheter assembly 300.

Figure 8:
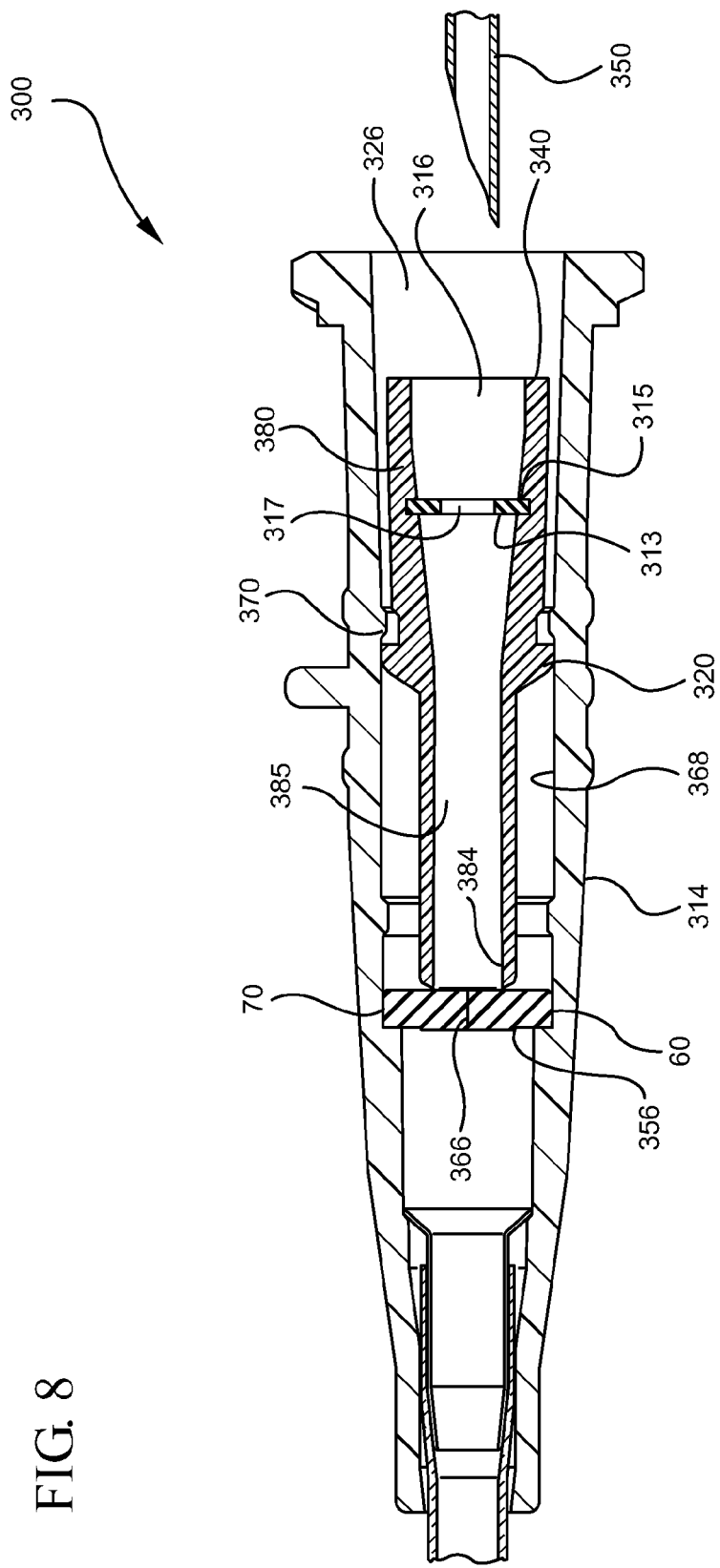
FIG. 8 is a cross-sectional view of an assembled over-the-needle catheter assembly in accordance with a representative embodiment, following removal of the introducer needle.

Referring now to FIG. 8, a cross-sectional view of catheter assembly 300 is shown following removal of introducer needle 350. Upon removal of introducer needle 350, the slit 366 of septum 356 is no longer biased open and therefore recloses and seals to prevent flow of fluids and/or air via the slit 366. The hole 317 of the cavity seal 315 remains open to serve a fluid channel during septum activation. As previously discussed, during removal, any blood flowing through the forward chamber 362 and through the introducer needle 350 is captured and retained in the internal cavity 385 to prevent blood exposure through the proximal end 326 of the catheter assembly 300. In some embodiments, the slit 366 includes a leak orifice (not shown) to permit controlled flow between the forward and rearward chambers 362 and 364. In other embodiments, a plurality of ventilation channels 70 are provided between the outer surface of the septum 356 and the septum channel 60.

Figure 9:
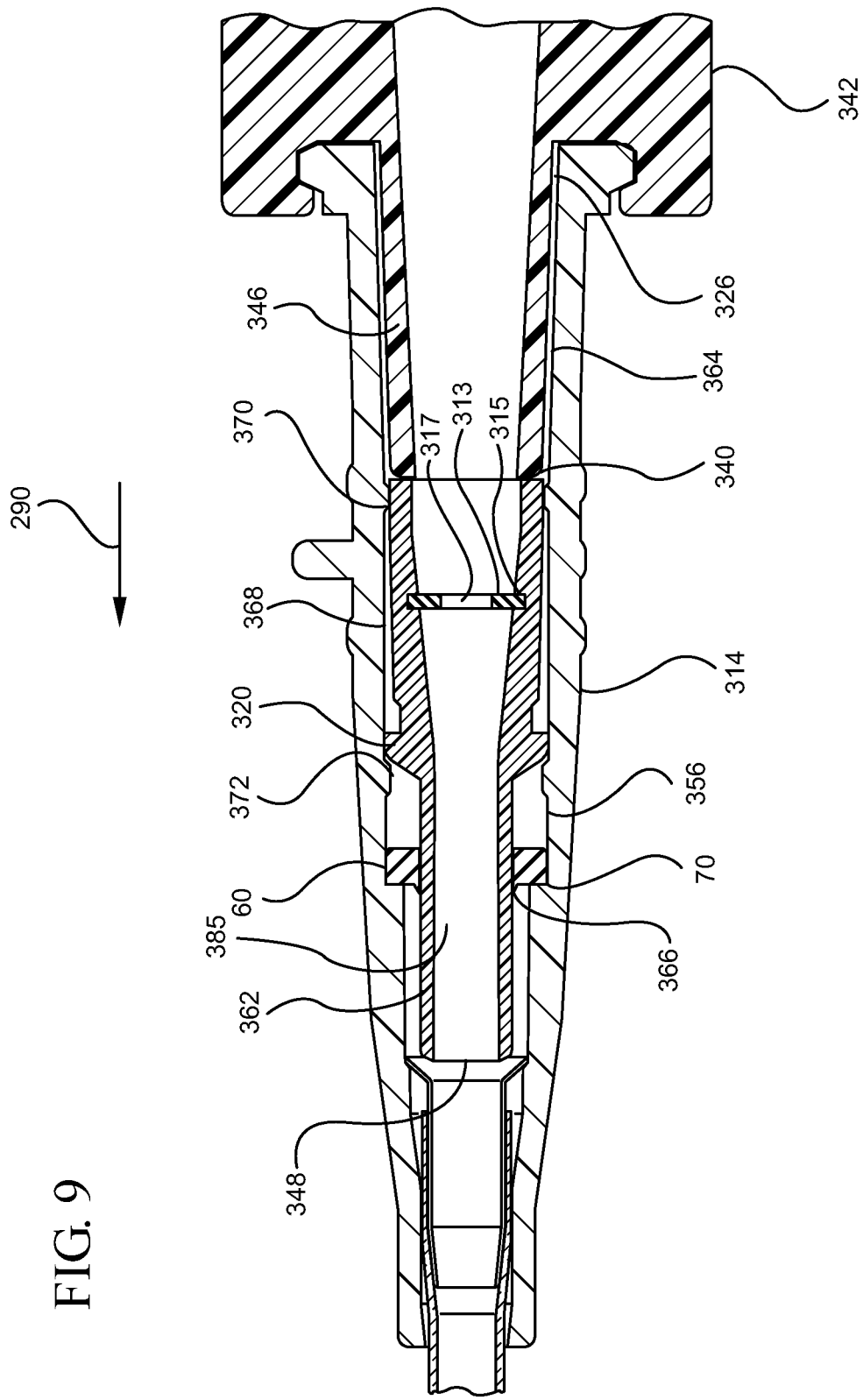
FIG. 9 is a cross-sectional view of an assembled over-the-needle catheter assembly in accordance with a representative embodiment, following activation.

Referring now to FIG. 9, a cross-sectional view of catheter assembly 300 is shown following activation of septum 356 via septum activator 380. Upon insertion of a coupler 342 into the proximal opening 326 of the catheter adapter 314, the probe portion 346 of the coupler 342 contacts the contact surface 340 of septum activator 380. Septum activator 380 is accordingly advanced in a distal direction 390 as the coupler 342 is further inserted into proximal opening 326 thereby causing flushing fins 320 to translate within translating groove 368. As coupler 342 is advanced further into the proximal opening 326, probing surface 348 of the septum activator 380 passes through the slit 366 of septum 356. As such, the probing surface 348 of the septum activator 380 is positioned within the forward chamber 362 providing a fluid pathway through the septum 356.

Figure 10:
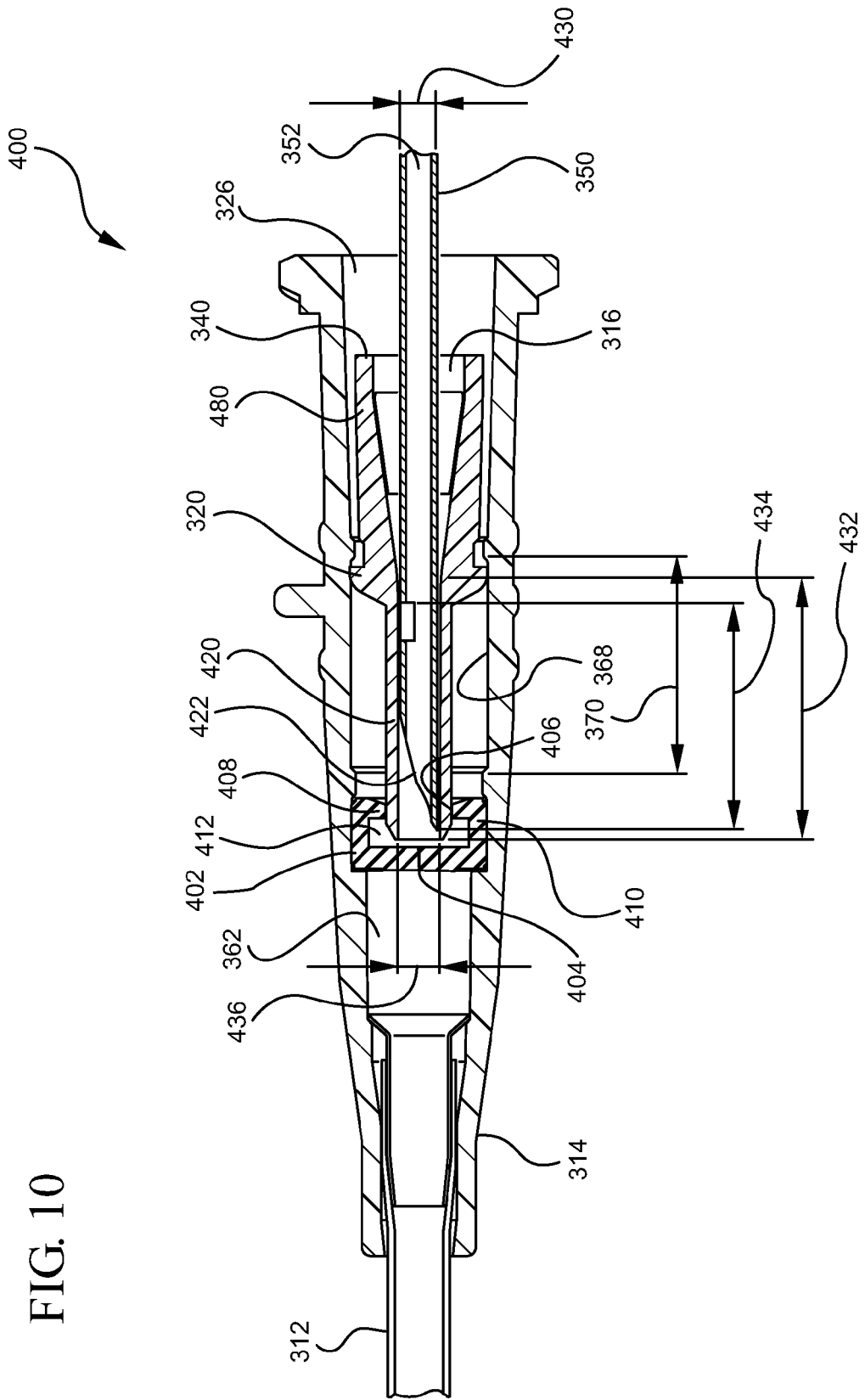
FIG. 10 is a cross-sectional view of another over-the-needle catheter assembly in accordance with another representative embodiment.

FIG. 10 illustrates a cross-sectional view of another embodiment of a catheter assembly 400 that is similar to that of FIG. 9 but has a modified septum activator 480 and septum 402. FIG. 10 is shown following removal of the introducer needle 350 and prior to activation of the septum 402. As shown, the distal part of the septum activator 480 comprises a sleeve portion 420 that spans the distance 432 and included the part of the septum activator 480 that forms a sleeve around the needle and has an internal diameter 436 approximately equal to the external diameter 430 of the introducer needle 350. This sleeve portion 420 begins at the distal tip of the septum activator 480 and extends proximally for a distance 432. This distance 432 is greater than the notch distance 434 so that the sleeve portion 420 prevents blood within forward chamber 362 from defeating the septum 402 by flowing through the orifice in the needle tip and out the needle notch when the needle tip is distal the septum and the needle notch is proximal the septum. Thus, the sleeve portion 420 of the septum activator 480 can decrease blood exposure during needle withdrawal.

FIG. 10 also illustrates an alternative embodiment of a septum 402 that can be utilized with at least some of the embodiments of catheter assemblies illustrated and discussed previously. As shown, the septum 402 includes a distal barrier having a slit 404. In some embodiments, the distal barrier forms a disk. An annular ridge 410 extends proximally from the distal barrier. In some embodiments, the annular ridge includes an inward extension 408 that extends inward and forms an inner diameter substantially equal to the outer diameter of the distal portion of the septum activator 480. In other embodiments, the annular ridge 410 has an inner diameter substantially equal to the outer diameter of the distal portion of the septum activator 480. In some embodiments, an inner chamber 412 is formed between the septum 402 and the septum activator 480 when the septum activator is in the pre-activated position. Thus configured, the septum is disposed and forms a seal between the body of the catheter adapter 314 and the septum activator 480. This seal prevents blood within the septum activator from leaking into the space between the septum activator and the body of the catheter adapter 314 during and after needle withdrawal. Accordingly, the combination of the sleeve portion 420 of the septum activator 480 and the geometry of the septum 402 can prevent, is at least partially, blood from exiting through the proximal end of the catheter assembly 400 following needle.

As illustrated, the septum 402 contacts the septum activator 480 at a contact surface 406. In some embodiment this contact provides a substantially fluid tight seal between the distal end of the septum activator 480 and the septum. Thus sealed, blood within the septum activator 480 or the septum 402 can not escape through this contact surface 406.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A catheter assembly, comprising:
 a catheter adapter having an inner lumen, the inner lumen including an annular ridge;
 a septum disposed within a portion of the inner lumen;
 an introducer needle extending through the inner lumen of the catheter adapter, the introducer needle having an outer diameter, the introducer needle having a notch disposed on the distal end of the introducer needle, the notch being positioned at a notch distance from a distal tip of the introducer needle; and
 a septum activator disposed within the inner lumen of the catheter adapter proximal to the septum, the septum activator comprising a sleeve portion and a proximal portion, the sleeve portion forming a distal portion of the septum activator, the sleeve portion comprising an inner lumen having an internal diameter approximately equal to the outer diameter of the introducer needle along the length of the sleeve portion, the septum activator further including one or more flushing fins positioned on an outer surface of the septum activator so as to contact the annular ridge to limit the proximal movement of the septum activator, the annular ridge being positioned such that the distal end of the septum activator remains in contact with the septum when in a proximal-most position, the sleeve portion having a length greater than the notch distance so that, when the introducer needle is withdrawn proximally, the notch remains contained within the sleeve portion until after the distal tip of the introducer needle is drawn through the septum and into the sleeve portion.

2. The catheter assembly of claim 1, wherein the septum includes a seal interposed between an outer surface of the sleeve portion of the septum activator and an inner surface of the septum.

3. The catheter assembly of claim 2, wherein the inner surface of the septum is an inner chamber.

4. The catheter assembly of claim 3, wherein the inner chamber is present prior to activation of the catheter assembly.

5. The catheter assembly of claim 1, wherein a proximal end of the septum further comprises an annular ridge that extends inward, the annular ridge having an inner diameter substantially equal to the outer diameter of the septum activator.

6. A catheter assembly comprising:
  a catheter adapter having an inner lumen, the inner lumen including an annular ridge that defines a translating groove;
  a septum disposed within the inner lumen distal to the translating groove, the septum including a distal barrier and an annular ridge that includes an inward extension;
  a septum activator disposed within the inner lumen proximal to the septum, the septum activator having a sleeve portion at a distal end, the sleeve portion having an outer diameter that is substantially the same as the inner diameter of the inward extension thereby forming a seal between the sleeve portion and the inward extension of the septum, the septum activator including one or more flushing fins that extend from an outer surface of the septum activator, the septum activator being positioned with the one or more flushing fins distal to the annular ridge of the inner lumen such that when the septum activator slides within the translating groove, the annular ridge contacts the one or more flushing fins to limit the proximal movement of the septum activator, wherein the sleeve portion of the septum activator has a length that causes a distal end of the septum activator to be contained within the inward extension of the septum proximal to the distal barrier when the one or more flushing fins contact the annular ridge of the inner lumen; and
  an introducer needle having an outer diameter that is substantially the same as the inner diameter of the sleeve portion of the septum activator, the introducer needle including a notch at a distance from a distal tip of the introducer needle that causes the notch to be contained within the sleeve portion when the distal tip of the introducer needle is positioned proximal to the distal barrier of the septum.

7. The catheter assembly of claim 6, wherein the inward extension of the septum is spaced from the distal barrier thereby forming an inner chamber for collecting blood that flows out from the distal tip of the introducer needle when the introducer needle is positioned proximal to the distal barrier of the septum, and wherein the seal between the inward extension and the sleeve portion prevents the blood from exiting the inner chamber.

8. The catheter assembly of claim 7, wherein the distance between the notch and the distal tip of the introducer needle is less than the length of the sleeve portion of the septum activator.

9. The catheter assembly of claim 7, wherein the inner lumen includes a distal annular ridge that defines a distal end of the translating groove, the distal annular ridge contacting the one or more flushing fins to limit the distal movement of the septum activator.

10. The catheter assembly of claim 7, wherein the septum activator includes a proximal portion that has an inner diameter that is greater than the inner diameter of the sleeve portion.

11. The catheter assembly of claim 10, wherein an outer diameter of the proximal portion of the septum activator is greater than the outer diameter of the sleeve portion.

12. The catheter assembly of claim 7, wherein the distal barrier of the septum includes one or more slits.

13. A catheter assembly comprising:
  a catheter adapter;
  a septum disposed within an inner lumen of the catheter adapter, the septum having a C-shaped cross-section that includes a distal barrier and an inward extension positioned proximal to the distal barrier to form an inner chamber, the inward extension having a first inner diameter;
  a septum activator disposed within the inner lumen of the catheter adapter, the septum activator having a sleeve portion forming a distal end that is contained within the inner chamber, the sleeve portion having a first outer diameter that is substantially the same as the first inner diameter thereby forming a seal to prevent blood from flowing proximally out of the inner chamber, the septum activator further including one or more flushing fins that contact an annular ridge formed in the inner lumen to limit the proximal movement of the septum activator, wherein when the one or more flushing fins contact the annular ridge, the distal end of the sleeve portion is contained within the inner chamber; and
  an introducer needle having an outer diameter that is substantially the same as an inner diameter of the sleeve portion thereby preventing blood from flowing within the septum activator between an inner surface of the septum activator and an outer surface of the introducer needle.

14. The catheter assembly of claim 13, wherein the introducer needle includes a notch.

15. The catheter assembly of claim 14, wherein the notch is positioned at a distance from a distal tip of the introducer needle that is less than the length of the sleeve portion.

* * * * *